(12) United States Patent
Zhang et al.

(10) Patent No.: US 9,969,695 B2
(45) Date of Patent: May 15, 2018

(54) N-SUBSTITUTED IMIDAZOLE CARBOXYLIC ESTER CHIRAL COMPOUND CONTAINING AN ETHER SIDE CHAIN, ITS PREPARATION AND APPLICATION

(71) Applicant: WEST CHINA HOSPITAL, SICHUAN UNIVERSITY, Chengdu, Sichuan (CN)

(72) Inventors: Wensheng Zhang, Sichuan (CN); Jun Yang, Sichuan (CN); Jin Liu, Sichuan (CN); Lei Tang, Sichuan (CN); Bowen Ke, Sichuan (CN)

(73) Assignee: WEST CHINA HOSPITAL, SICHUAN UNIVERSITY, Chengdu, Sichuan (CN)

( * ) Notice: Subject to any disclaimer, the term of this patent is extended or adjusted under 35 U.S.C. 154(b) by 0 days. days.

(21) Appl. No.: 15/107,415

(22) PCT Filed: Oct. 30, 2014

(86) PCT No.: PCT/CN2014/089898
§ 371 (c)(1),
(2) Date: Jun. 22, 2016

(87) PCT Pub. No.: WO2015/096551
PCT Pub. Date: Jul. 2, 2015

(65) Prior Publication Data
US 2017/0001963 A1    Jan. 5, 2017

(30) Foreign Application Priority Data

Dec. 23, 2013 (CN) .......................... 2013 1 0716377

(51) Int. Cl.
C07D 233/90 (2006.01)
A61P 25/20 (2006.01)
A61P 23/00 (2006.01)

(52) U.S. Cl.
CPC ........ C07D 233/90 (2013.01); C07B 2200/07 (2013.01)

(58) Field of Classification Search
CPC .......................... C07D 233/90; C07B 2200/07
See application file for complete search history.

(56) References Cited

U.S. PATENT DOCUMENTS 3,354,173 A * 11/1967 Godefroi .............. C07D 213/38 546/274.7
4,770,689 A *  9/1988 Van Gestel ............ A01N 43/50 504/253
9,181,197 B2 * 11/2015 Raines ................. C07D 233/90

FOREIGN PATENT DOCUMENTS

CN    102046607 A      5/2011
CN    103588757 A  *  2/2014

OTHER PUBLICATIONS

English Machine Translation of Yang et al. "N-substituted imidazole carboxylic ester compound with ultrashort-acting anesthetic effect, preparation method and use thereof." CN 103588757 A [retrieved on Jan. 27, 2017] Retrieved from the Internet <URL: https://worldwide.espacenet.com/>.*
Chankvetadze et al. "High performance liquid chromatography enantioseparation of chiral pharmaceuticals using tris(chloromethylphenylcarbamate)s of cellulose" J. Ph. Biomed. Anal. 1996, 14, 1295-1303.*
Ri Le Ge et al,; "Pharmacological Studies of Methoxycarbonyl Etomidate"s Carboxylic Acid Metabolite", Anesth Analg, vol. 115, No. 2, Aug. 31, 2012, pp. 305-308.
Maria Erlandsson et al; "Synthesis and in Vitro Evaluation of 18F-Labelled Di-and Tri (Ethylene Glycol) Metomidate Esters", Journal of Labelled Compounds and Radiopharmaceuticals, vol. 52, Apr. 1, 2009, pp. 278-285.
S. Shaukat Husain et al.;"Synthesis of Trifluoromethylaryl Diazirine and Benzophenone Derivatives of Etomidate that are Potent General Anesthetics and Effective Photolabels for Probing Sites on Ligand-Gated Ion Channels"; J. Med. Chem.; vol. 49, 2006; pp. 4818-4825.
Ilse M. Zolle et al.; "New Selective Inhibitors of Steroid 11-Hydroxylation in the Adrenal Cortex. Synthesis and Structure—Activity Relationship of Potent Etomidate Analogues"; J. Med. Chem.; vol. 51, 2008, pp. 2244-2253.
Stuart A. Forman; "Clinical and Molecular Pharmacology of Etomidate", Anesthesiology; Mar. 2011, vol. 114(3), pp. 695-707.
Joseph F. Cotten et al., "Methoxycarbonyl-etomidate: A Novel Rapidly Metabolized and Ultra-Short Acting Etomidate Analogue That Does Not Produce Prolonged Adrenocortical Suppression", Anesthesiology, vol. 111, No. 2, Aug. 31, 2009, pp. 240-249.

(Continued)

*Primary Examiner* — Amanda L Aguirre
(74) *Attorney, Agent, or Firm* — Novick, Kim & Lee, PLLC; Allen Xue

(57) ABSTRACT

The present invention relates to an N-substituted imidazole carboxylic ester chiral compound containing an ether side chain and to its preparation and application. The structure of this compound is represented by Formula (I). This compound can induce a rapid and reversible general anesthesia effect. Animal experiments show that this compound has rapid and short-acting pharmacological characteristics, so that it can be used as a rapid and short-acting general anesthesia medicine. Compared with etomidate, this compound can reduce the inhibition on the synthesis of adrenal cortical hormone, with an advantage of rapid and full recovery of the post-operative patient. The only chiral carbon in the compound structure belongs to the R form. This imidazole ring in the compound structure has acidifiable N atoms, so that this compound or its related pharmaceutically-acceptable salts can be used in preparation of the central inhibitory medicines, which can produce sedative, hypnotic and/or anesthetic effects on animals or human beings via their intravenous or non-intravenous administration.

(I)

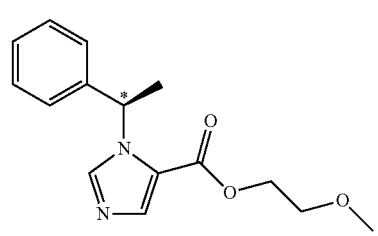

6 Claims, 2 Drawing Sheets

(56) References Cited

OTHER PUBLICATIONS

S. Shaukat Husain, D.P. et al., "Modifying Methoxycarbonyl Etomidate's Inter-Ester Spacer Optimizes in Vitro Metabolic Stability and in Vivo Hypnotic Potency and Duration of Action", Anesthesiology, vol. 117, No. 5, Nov. 30, 2012, pp. 1027-1036.

* cited by examiner

N-SUBSTITUTED IMIDAZOLE CARBOXYLIC ESTER CHIRAL COMPOUND CONTAINING AN ETHER SIDE CHAIN, ITS PREPARATION AND APPLICATION

TECHNICAL FIELD

The present invention relates to N-substituted imidazole carboxylic ester chiral compound containing an ether side chain and to its preparation and application.

BACKGROUND

Etomidateis a commercially-available medicine used for general intravenous anesthesia for a long time. As it acts rapidly and lasts for a short time, etomidate is a desirable medicine inducing general intravenous anesthesia. Etomidate has a unique pharmacological action on cardiovascular stability, causing a minimal suppression on systematic circulation when compared with the other general anesthetic medicines. Therefore, etomidate is particularly suitable in operation for patients with cardiac dysfunction (Cotton J F, Anesthesiology 2009; 111: 240). At present, the anesthetic mechanism of etomidate has already been identified. It induces anesthetic effects mainly by its binding to central inhibitory receptor $GABA_A$, making this receptor more sensitive to GABA. However, further researches have indicated that etomidate has an inhibitory action on synthesis of cortical hormone in the body; especially during a prolonged continuous infusion, the inhibitory action becomes more obvious (Husain S S, J Med Chem 2006; 49: 4818-4825). Self-synthesis of cortical hormone is an important anti-inflammatory factor, and thus this shortcoming is unfavorable for recovery of the post-operative patient. As the unfavorable effect is gradually verified by clinical investigation, its use has gradually decreased in frequency. The suppression of etomidate on adrenal cortex hormone is mainly caused by its inhibiting the activity of 11β-hydroxylase. This enzyme is critical for cortical hormone synthesis. This unfavorable effect of etomidate is related to the imidazole structure in the medicinal molecule, and one N atom in the imidazole ring can form complexation with topological iron atom, thus strengthening the binding of medicinal molecules to the enzyme molecules. Thus, 11β-hydroxylase is inhibited. Moreover, the ability of etomidate binding to 11β-hydroxylase is 100 times stronger than that binding to $GABA_A$ acceptor. These finding shave brought an challenge to the designing of the imidazole derivatives, which should have no or weaker ability of binding to 11β-hydroxylase (Zolle I M, J Med Chem 2008; 51: 2244-2253). Etomidate is mainly metabolized in the liver. Based on the metabolic investigation, a time/effect curve has been drawn concerned with therapeutic effect and adverse effect for the etomidate use (Forman S A, Anesthesiology 2011; 114(3): 695-707). This curve has indicated that after one intravenous bolus of etomidate 3 mg/kg, the minimal effective concentration of anesthetic effect is 110 ng/ml, and the time for the plasma medicine concentration maintaining above 3 mg/kg is only 8 min, while the minimal effective concentration of etomidate for inhibition of cortical hormone synthesis is 8 ng/ml, and the plasma medicine concentration maintaining above 8 ng/mL is up to 8 h. These findings have indicated that when the patients are given an anesthetic dosage of etomidate, the inhibitory action on cortical hormone synthesis will be kept for a longer time after a fast loss of anesthetic effects.

Therefore, to obtain a better imidazole-type general anesthetic medicine that does not inhibit cortical hormone synthesis but retains pharmacological activity of etomidate is very important.

Contents of the Invention

The present invention provides an N-substituted imidazole carboxylic ester chiral compound containing an ether side chain and provides its preparation and application.

According to the present invention, the N-substituted 1H-imidazole-5-carboxylate chiral compounds include the pharmaceutically-acceptable salts of the chiral compound. The structure of the N-substituted imidazole carboxylic ester chiral compound is shown in Formula (I), where the configuration of chiral carbon C* belongs to the R form.

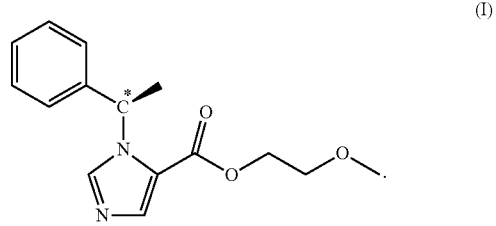 [SMILES: COCCOC(=O)c1cncn1[C@H](C)c1ccccc1]

The pharmaceutically-acceptable salts related to the N-substituted imidazole carboxylic ester chiral compound include the commonly-used salts in the field of pharmacy, such as hydrochloride, hydrobromide and trifluoroacetate.

This kind of salt compounds can be obtained by optical resolution of their enantiomers or by direct preparation. In the polar aprotic solvent and at the presence of base substance, the target compound (Formula (I)) can be produced by substitution reaction of N-substituted imidazole carboxylic acid chiral compound (Formula (II)) with halide (Formula (III)). In Formulas (I) and (II), the configuration of chiral carbon C* belongs to the R form, and X is halogen. The reaction process is as follows:

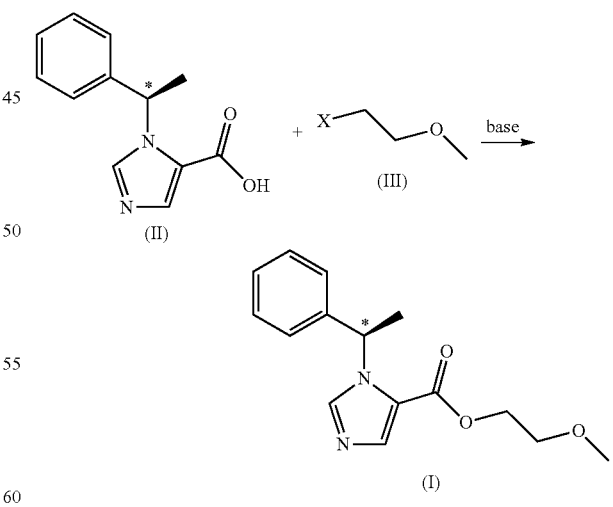

Based on the above-mentioned method, other preferable ways can be used separately or in combination, which are specified in the following:

The halogen is preferably Br or Cl; the reaction solvent is preferably DMF; the base is preferably an inorganic base, e.g., alkali metal hydroxides or carbonates.

The structure of the compound of Formula (I) contains a basic N atom capable of forming the pharmaceutically-acceptable salts. The Formula (I) compound obtained by the above-mentioned preparation method or other ways can be combined with pharmaceutically-acceptable acid radicals to obtain the corresponding salts.

Guided by the present invention, the results of the animal experiments have shown that the N-substituted imidazole carboxylic ester compound of Formula (I) and its salts can induce fast and reversible pharmacologic actions such as sedative-hypnotic and/or anesthetic effects. Compared with etomidate, the single administration of the compounds can maintain a shorter anesthetic time, a more short-acting anesthetic effect and a better palinesthesia. It also can obviously decrease the inhibition on adrenocortical hormone and produce rapid and full recovery of the post-operative patient. The potency and the safety range of the corresponding (9-optical isomer (IV) and racemate (V) of the Formula (I) compound are obviously inferior to those of the R-form Formula (I) compound (including the pharmaceutically-acceptable salts). Thus, the N-substituted imidazole carboxylic ester chiral compound and the pharmaceutically-acceptable salts have an obvious advantage when they are used in preparation of central inhibitory medicines, which can generate better sedative, hypnotic and/or anesthetic effects on animals or human beings via their intravenous or non-intravenous administration.

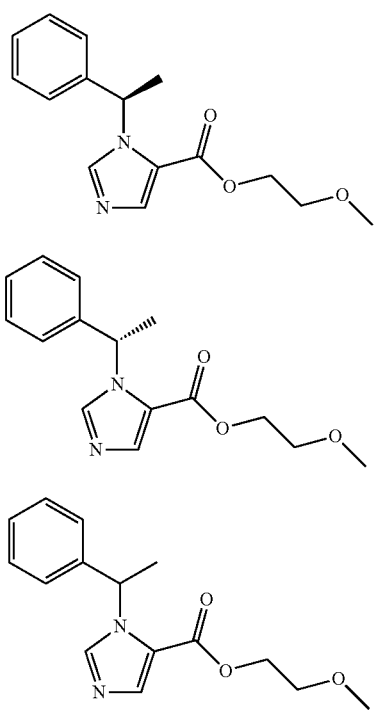

The above contents concerned with the present invention will be illustrated in detail by the following examples as shown in the figures. However, it should not be considered that the scope of the present invention is only limited to the following examples. Guided by the present invention, all the substitutions or modifications should be included in the scope of the present invention.

EXAMPLES

Example 1

Preparation of the Formula (I) Compound Guided by the Present Invention

The compound of Formula (II) (CAS: 56649-48-0) (216 mg, 1 mmol), the compound of Formula (III) (CAS:6482-24-2) (278 mg, 2 mmol), and anhydrous potassium carbonate (564 mg, 3 mmol) were mixed and added in 15 mL of N,N-dimethylformamide, and the mixture was stirred at 50° C. and reacted overnight. Next day, the reaction solution was poured into 100 mL of cold water to obtain a clear solution, and was then extracted with ethyl acetate for three times (50 mL for each time). The combined organic layer was dried with anhydrous sodium sulfate and filtered to give the filtrate. Evaporation of the solvent under the reduced pressure provided oily crude products. After purification by silica gel column (eluent: cyclohexane/ethyl acetate=3/2), colorless oily product (150 mg) was obtained, with a yield of 54%.

1) NMR: apparatus: Bruker, internal standard substance: TMS $^1$H-NMR (400 MHz CDCl$_3$) δ: 1.862 (3H, d, J=7.2 Hz), 3.393 (3H, s), 3.645 (3H, t, J=4.8 Hz), 4.31~4.405 (2H, m), 6.348 (1H, q, J=7.2 Hz), 7.17~7.359 (m, 5H), 7.742 (s, 1H), 7.827 (s, 1H).

$^{13}$C-NMR (100 MHz CDCl$_3$) δ: 22.30, 55.48, 59.15, 63.53, 70.48, 122.39, 126.36, 128.08, 128.93, 138.63, 140.02, 141.20, 160.26.

2) MS: mass spectrometer: API3000 LC-Ms/Ms from American ABI company; ionization mode: ESI.

(M+H).HRMS: for C$_{15}$H$_{18}$N$_2$O$_3$+H, calcd 275.1396, found 275.1396.

3) Optical rotation value: The ethanol solution of the compound of Formula (I) was prepared at a concentration of 1 g/100 mL, and [α]D$^{20}$ value was measured using Polarimeter 341 polarimeter, with [α]$_D^{20}$=+71.9°.

Figure 1:
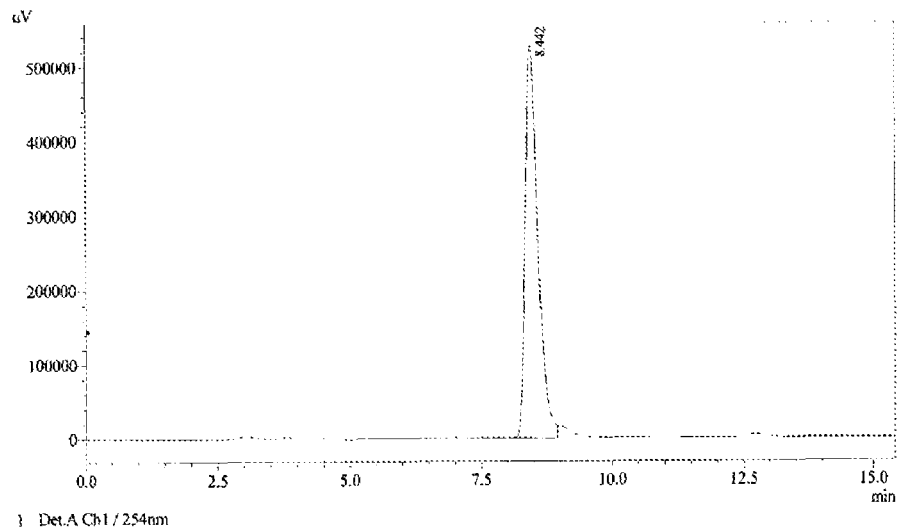
FIG. 1 is the detection graph of the ee value for the product of Example 1 (Formula (I) compound).

4) The ee value: The compound of Formula (I) was dissolved in methanol at a concentration of 1 mg/mL and then diluted 100 times before injection. The detection was performed by HPLC using chiral AD column, wavelength of UV detector: 254 nm, mobile phase: 20% isopropanol-n-hexane, flow rate: 1 mL/min. The optical purity of the compound of Formula (I) was determined to be 100% (FIG. 1).

Example 2

Preparation of the Formula (I) Compound Guided by the Present Invention

The compound of Formula (II) (CAS: 56649-48-0) (216 mg, 1 mmol), the compound of Formula (III) (CAS:627-42-9) (188 mg, 2 mmol), and anhydrous potassium carbonate (564 mg, 3 mmol) were mixed and added in 15 mL of N,N-dimethylformamide, and the mixture was stirred at 50°

C. and reacted overnight. Next day, the reaction solution was poured into 100 mL of cold water to obtain a clear solution, and was then extracted with ethyl acetate for three times (50 mL for each time). The combined organic layer was dried with anhydrous sodium sulfate and filtered to give the filtrate. Evaporation of the solvent under the reduced pressure provided oily crude products. After purification by silica gel column (eluent: cyclohexane/ethyl acetate=3/2), colorless oily product (120 mg) was obtained, with a yield of 43%.

Example 3

Preparation of (S)-Optical Counterpart Compound (IV)

The compound of S-(−)-1-(1-phenethyl)-1-H-imidazole-5-carboxylic acid (CAS:56649-49-1) (216 mg, 1 mmol), the compound of Formula (III) (CAS:627-42-9) (188 mg, 2 mmol), and anhydrous potassium carbonate (564 mg, 3 mmol) were mixed and added in 15 mL of N,N-dimethylformamide, and the mixture was stirred at 50° C. and reacted overnight. Next day, the reaction solution was poured into 100 mL of cold water to obtain a clear solution, and was then extracted with ethyl acetate for three times (50 mL for each time). The organic layers were combined, dried with anhydrous sodium sulfate, and filtered to give the filtrate. Evaporation of the solvent under the reduced pressure provided oily crude products. After purification by silica gel column (eluent: cyclohexane/ethyl acetate=3/2), colorless oily product (170 mg) was obtained, with a yield of 61.2%.

1) NMR: apparatus: Bruker, internal standard substance: TMS $^1$H-NMR (400 MHz CDCl$_3$) δ: 1.859 (3H, d, J=7.2 Hz), 3.392 (3H, s), 3.644 (3H, t, J=4.8 Hz), 4.30~4.412 (2H, m), 6.342 (1H, q, J=7.2 Hz), 7.17~7.355 (m, 5H), 7.728 (s, 1H), 7.822 (s, 1H).

2) Optical rotation value: The ethanol solution of the compound of Formula (IV) was prepared at a concentration of 1 g/100 mL, and the $[α]_D^{20}$ value was measured using Polarimeter 341 polarimeter, with $[α]_D^{20}$=+69.3°.

Figure 2:
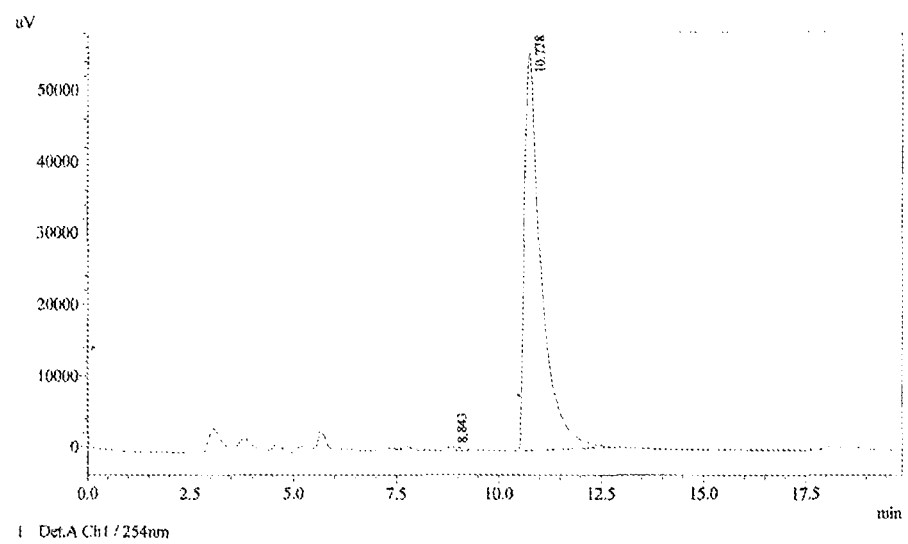
FIG. 2 is the detection graph of the ee value for the product of Example 3 (Formula (IV) compound).
Figure 3:
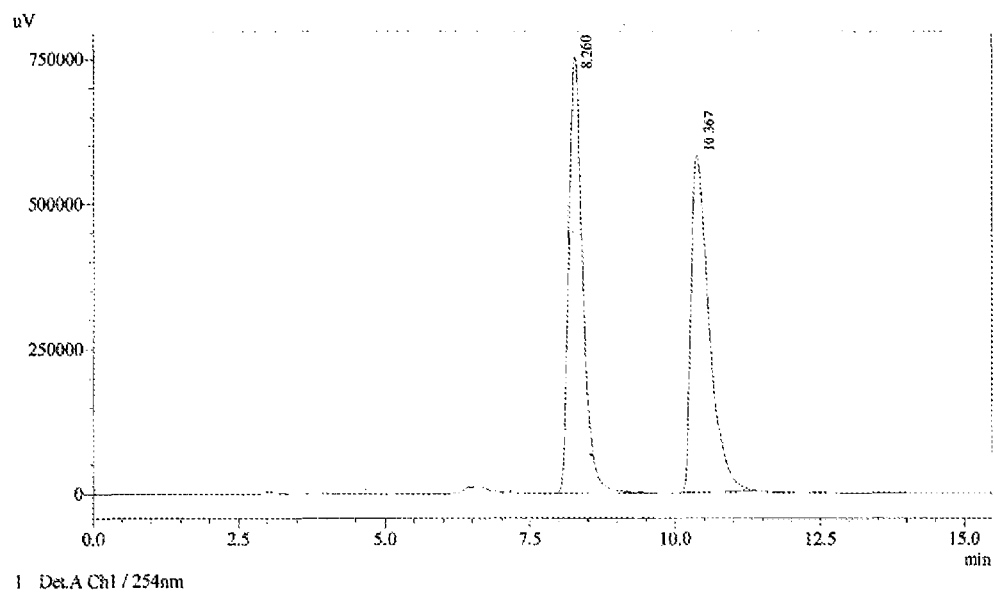
FIG. 3 is the detection graph of the ee value for the product of Example 4 (Formula (V) compound).

3) The ee value: The compound of Formula (IV) was dissolved in methanol at a concentration of 1 mg/mL and then diluted 100 times before injection. The detection was performed by HPLC using chiral AD column, wavelength of UV detector: 254 nm, mobile phase: 20% isopropanol-n-hexane, flow rate: 1 mL/min. The optical purity of the Formula (IV) compound was determined to be 99% (FIG. 2).

Example 4

Preparation of the Corresponding Racemic Compound (V)

The compound of (±)-1-(1-phenethyl)-1H-imidazole-5-carboxylic acid (CAS:7036-56-8) (216 mg, 1 mmol), the compound of Formula (III) (CAS:627-42-9) (188 mg, 2 mmol), and anhydrous potassium carbonate (564 mg, 3 mmol) were mixed and added in 15 mL of N,N-dimethylformamide, and the mixture was stirred at 50° C. and reacted overnight. Next day, the reaction solution was poured into 100 mL of cold water to obtain a clear solution, and was then extracted with ethyl acetate for three times (50 mL for each time). The organic layers were combined, dried with anhydrous sodium sulfate, and filtered to give the filtrate. Evaporation of the solvent under the reduced pressure provided oily crude products. After purification by silica gel column (eluent: cyclohexane/ethyl acetate=3/2), colorless oily product (170 mg) was obtained, with a yield of 63.7%.

1) NMR: apparatus: Bruker, Internal standard substance: TMS $^1$HNMR (300 MHz CDCl$_3$) δ: 1.839 (3H, d, J=7.2 Hz), 3.384 (3H, s), 3.619 (2H, t, J=4.8 Hz), 4.28~4.388 (2H, m), 6.325 (1H, q, J=7.2 Hz), 7.15~7.344 (m, 5H), 7.749 (s, 1H), 7.806 (s, 1H).

2) The ee value: The compound of Formula (V) was dissolved in methanol at a concentration of 1 mg/mL and then diluted 100 times before injection. The detection was performed by HPLC using chiral AD column, wavelength of UV detector: 254 nm, mobile phase: 20% isopropanol-n-hexane, flow rate: 1 mL/min. The compound of Formula (V) was a mixture of R and S configurations at an equal ratio, i.e. the racemate.

Example 5

The product of Example 1 (2 g) was dissolved in 50 mL of anhydrous diethyl ether; in ice bath, excess HCl gas was introduced; then, a lot of white precipitate was obtained. After filtration and drying, white powders (1.97 g) were obtained, i.e. hydrochloride of the Formula (I) compound. NMR: apparatus: Bruker, Internal standard substance: TMS.

$^1$HNMR (300 MHz D$_2$O) δ: 1.833 (3H, d, J=7.2 Hz), 3.378 (3H, s), 3.614 (2H, t, J=4.8 Hz), 4.28~4.392 (2H, m), 6.321 (1H, q, J=7.2 Hz), 7.33~7.452 (m, 5H), 8.001 (s, 1H), 9.908 (s, 1H).

Example 6

The product of Example 1 (2 g) was dissolved in 50 mL of anhydrous diethyl ether, 10% acetic acid solution of HBr was added dropwise in ice bath, and then a lot of white precipitate was obtained. After filtration and drying, white powders (2.12 g) were obtained, i.e. hydrobromide of the Formula (I) compound. NMR: apparatus: Bruker, Internal standard substance: TMS.

$^1$HNMR (300 MHz D$_2$O) δ: 1.821 (3H, d, J=7.2 Hz), 3.358 (3H, s), 3.611 (2H, t, J=4.8 Hz), 4.28~4.398 (2H, m), 6.319 (1H, q, J=7.2 Hz), 7.34~7.467 (m, 5H), 8.000 (s, 1H), 9.907 (s, 1H).

Example 7 (Trifluoroacetate Example)

The product of Example 1 (2 g) was dissolved in 50 mL of anhydrous diethyl ether, equal molar of trifluoroacetic acid was added dropwise in ice bath, and then a lot of white precipitate was obtained. After filtration and drying, white powders (1.87 g) were obtained, i.e. trifluoroacetate of the Formula (I) compound. NMR: apparatus: Bruker, Internal standard substance: TMS.

$^1$HNMR (300 MHz D$_2$O) δ: 1.842 (3H, d, J=7.2 Hz), 3.367 (3H, s), 3.609 (2H, t, J=4.8 Hz), 4.27~4.382 (2H, m), 6.331 (1H, q, J=7.2 Hz), 7.31~7.432 (m, 5H), 8.011 (s, 1H), 9.928 (s, 1H).

Example 8

Male SD rats (250~300 g) were used as an experimental animal, and 50% effective dose ($ED_{50}$) was determined by the sequential method. Three compounds were dissolved in a solvent of DMSO, and etomidate was used as the commercially-available formulation (B BRAUN, Etomidate-Lipuro®, 20 mg/10 mL). Based on the initial dose of 1 mg/kg, other dosages were adjusted as the ratio of 0.8, and the $ED_{50}$ values of the three compounds and etomidate were determined. Extinction time ≥30 s for the rat body-righting reflex was the positive marker while no disappearance of the righting reflex was considered invalid. Based on the experimental results, four cross-points were formed, and the $ED_{50}$ values were calculated. The results indicated that the $ED_{50}$ values of the three compounds and etomidate were 2.10 mg/kg, 7.46 mg/kg, 10.38 mg/kg and 1.14 mg/kg, respectively. Then, the respective $2ED_{50}$ values of the three compounds and etomidate were taken in an equivalent dose, which were administered via the rat tail vein. The preliminary effects were evaluated in the four rat groups, which were given the three compounds of Formulas (I), (IV), (V) and etomidate, respectively, with 10 rats in each group. The experimental results showed that after administration, the Formula (I) compound and etomidate produced an immediate action, but the Formulas (IV) and (V) compounds produced a little slower action. The last time of the Formula (I) compound and etomidate was 5-6 min, but the last time of the Formulas (IV) and (V) compounds was 10-20 min. During the test period, types and incidence rates of the adverse effects produced by the compounds of Formulas (IV) and (V) were obviously increased. DMSO had no pharmacological effects, and no adverse effects were observed. The onset time, the last time, and the adverse effects (types, incidence rates) induced by the three compounds and etomidate are shown in the following table:

Above-mentioned results from the animal experiments have shown that the R-form compound of Formula (I) and etomidate have good sedative-hypnotic and general anesthetic effects, but the S-form enantiomeric compound of Formula (IV) and racemic compound of Formula (V) have lower potency, elongated onset time, extended last time, and increased types and incidence rates of adverse effects.

Example 9

Male SD rats (250~300 g) were used as an experimental animal, and 50% effective dose ($ED_{50}$) was determined by the sequential method. Hydrochlorides of the three compounds were dissolved in the solvent of normal saline, and etomidate was used as the commercially-available formulation (B BRAUN, Etomidate-Lipuro®, 20 mg/10 mL). The initial dose was 1 mg/kg, and the ratio of dosage variation was 0.8, which was applied in the determination of $ED_{50}$ values of Formula (I) hydrochloride, Formula (I) hydrobromide, Formula (I) trifluoroacetate, and etomidate. Extinction time (≥30 s) of the rat body-righting reflex was the positive marker while no disappearance of the reflex was considered invalid. Based on the experimental results, four cross-points were formed, and then $ED_{50}$ values were calculated. The $ED_{50}$ values of the three salts of Formula (I) and etomidate were 2.58 mg/kg, 3.09 mg/kg, 3.61 mg/kg, and 1.06 mg/kg, respectively. Then, the respective $2ED_{50}$ values of the three compounds and etomidate were taken in an equivalent dose,

TABLE 1

Onset time, last time, and adverse effects induced by three compounds and etomidate

| Compound | Onset time* (min) | Last time# (min) | Palinesthesia tune▲ (min) | Type, incidence of adverse effect (%) |
|---|---|---|---|---|
| DMSO | — | — | — | 0 |
| Etomidate | Immediate effect | 6.1 ± 1.3 | 4.5 ± 1.2 | Muscle tremor (7/10), 70% |
| Compound I | Immediate effect | 5.8 ± 0.9 | 4.8 ± 1.3 | Muscle tremor (7/10), 70% |
| Compound IV | 2.2 ± 0.8 | 20.3 ± 4.6 | 21.4 ± 2.3 | Muscle tremor (10/10), 100%; Vomiting (7/10), 70%; Anal sphincter dilatation (5/10), 50%; Hindlimb stiffness (5/10), 50%; Tic of limbs (7/10), 70%; Bucking (6/10), 60% |
| Compound V | 1.0 ± 0.6 | 10.8 ± 3.5 | 15.1 ± 2.6 | Muscle tremor (6/10), 60%; Vomiting (5/10), 50%; Anal sphincter dilatation (2/10), 20%; Hindlimb stiffness (2/10), 20%; Tic of limbs (5/10), 50%; Bucking (4/10), 40% |

Notes:
—: No pharmacological effect;
*Onset time denotes the time from completion of administration to appearance of body-righting reflex in experimental animals, and does not include the administration time of 30 s;
Last time denotes the time from disappearance of body-righting reflex to recovery of body-righting reflex in experimental animals;
▲Palinesthesia time denotes the time from recovery of body-righting reflex to full recovery of body-righting reflex in experimental animals.

which were administered via the rat tail vein. The preliminary effects were evaluated in the four rat groups, which were given the three compounds of Formulas (I) hydrochloride, Formula (I) hydrobromide, Formula (I) trifluoroacetate, and etomidate, respectively, with 10 rats in each group. After administration, Formula (I) hydrochloride, Formula (I) hydrobromide, Formula (I) trifluoroacetate, and etomidate produced an immediate action, and the last time was 5-7 min, 5-6 min, 4-7 min, and 4-8 min, respectively. Palinesthesia time was in arrange of 5-10 min. During the test period, no significant difference was found in the types and the incidence rates of adverse effects in each group. DMSO had no pharmacological effects, and no adverse effect was found. The onset time, the last time, and the types and the incidence rates of adverse effects induced by the three salt compounds and etomidate are shown in the following table:

TABLE 2

Onset time, last time, and types and incidence rates of adverse effects induced by three salt compounds and etomidate

| Compound | Onset time* (min) | Last time# (min) | Palinesthesia time▲ (min) | Type, incidence of adverse effect (%) |
|---|---|---|---|---|
| DMSO | — | — | — | 0 |
| Etomidate | Immediate | 5.9 ± 1.5 | 5.1 ± 1.3 | Muscle tremor (6/10), 60% |
| Hydrochloride of Formula (I) compound | Immediate | 5.8 ± 0.7 | 5.6 ± 1.8 | Muscle tremor (6/10), 60% |
| Hydrobromide of Formula (I) compound | Immediate | 4.6 ± 1.1 | 5.8 ± 1.2 | Muscle tremor (5/10), 50% |
| Trifluoroacetate of Formula (I) compound | Immediate | 3.6 ± 1.3 | 8.2 ± 3.3 | Muscle tremor (5/10), 50% |

Notes:
—: No pharmacological effect;
*Onset time denotes the time from completion of administration to appearance of body-righting reflex in experimental animals, and does not include the administration time of 30 s;
Last time denotes the time from disappearance of body-righting reflex to recovery of body-righting reflex in experimental animals;
▲Palinesthesia time denotes the time from recovery of body-righting reflex to full recovery of body-righting reflex in experimental animals.

Above-mentioned results from the animal experiments have shown that hydrochloride, hydrobromide and trifluoroacetate of the R-form compounds of Formula (I) and etomidate have good sedative-hypnotic and general anesthetic effects.

Example 10

Male Beagle dogs (10±2 kg) were selected as an experimental animal. After administration, the contents of corticosterone and cortisol in the blood serum of the Beagle dogs were determined by the ELISA kit and the enzyme-labelled instrument. The 20 Beagle dogs were divided into five groups, with four dogs in each group. After respective administration of dexamethasone (0.01 mg/kg), the level of adrenal cortex in the dog body was lowered to the baseline, and those levels of corticosterone and cortisol at this time were used as the base value (baseline). Then, the equivalent doses ($2ED_{50}$) of Formula (I) compound (2.88 mg/kg), Formula (IV) compound (5.66 mg/kg), Formula (V) compound (4.12 mg/kg), the positive control medicine Etomidate-Lipuro® (0.8 mg/kg), and equal-volume of solvent DMSO were respectively administered into the dogs of the five groups. After 10 min, ACTH (adrenocortical hormone) was given to stimulate and cause an increased level of cortex in the dog body. One hour after administration of ACTH, both corticosterone and cortisol levels in the blood serum of the Beagle dogs were determined, and the ratio of the peak value to the base value of the cortex levels was calculated. This ratio indicated the increase degree of the cortical hormone. A greater degree indicated a less inhibitory effect of the medicine on the cortical hormone. After administration, compounds of Formulas (I), (IV) and (V), DMSO, and the increase degree of the cortical hormone followed by stimulation of ACTH are shown in the following table:

TABLE 3

An increase degree of cortical hormone after administration of three compounds and stimulation of ACTH

| Compound | Increase degree of cortisol | Increase degree of corticosterone |
|---|---|---|
| DMSO | 40.25 ± 33.02 | 33.79 ± 12.4 |
| Etomidate | 2.12 ± 0.56 | 2.53 ± 0.65 |
| Compound (I) | 19.88 ± 19.8 | 11.46 ± 4.30 |
| Compound (IV) | 3.32 ± 2.36 | 1.19 ± 0.87 |
| Compound (V) | 5.17 ± 2.28 | 3.18 ± 1.15 |

The results from the above experiments have shown that etomidate can significantly inhibit the self-synthesis of adrenocortical hormone and make the cortex levels in the experimental dogs not increase after the stimulation by ACTH; the increased level in the dogs of the Formula (I) compound group was lower than that in the dogs of the blank group, but obviously higher than that of the dogs of the positive medicine etomidate group. Therefore, the inhibition of the Formula (I) compound on cortical hormone had already been obviously reduced when compared with that of the control medicine etomidate. Compared with the compounds of Formulas (IV) and (V), the Formula (I) compound produced an obviously lowered inhibitory effect on adrenocortical hormone.

Example 11

Male Beagle dogs (10±2 kg) were selected as an experimental animal. After administration, the contents of corticosterone and cortisol in the blood serum of the Beagle dogs were determined by the ELISA kit and the enzyme-labelled instrument. The 20 Beagle dogs were divided into five groups, with four dogs in each group. After respective administration of dexamethasone (0.01 mg/kg), the level of adrenal cortex in the dog body was lowered to the baseline, and the levels of corticosterone and cortisol at this time were used as the baseline. Then, the equivalent doses ($2ED_{50}$) of the compounds of Formula (I) hydrochloride (3.62 mg/kg), hydrobromide (3.86 mg/kg), trifluoroacetate (4.66 mg/kg), the positive control medicine Etomidate-Lipuro® (0.9 mg/kg), and the equal-volume of solvent DMSO were respectively administrated into the dogs of the five groups. After 10 min, ACTH was given to stimulate and cause the cortex levels increase in the dog body. One hour after administration of ACTH, both the cortical hormone levels were determined, and the ratio of the peak value to the baseline of cortex levels was calculated. This ratio indicated the increase degree of the cortical hormone. A greater degree of increase indicated a less inhibitory effect of the medicine on the cortical hormone. After administrations, the three salts of the Formula (I) compound, DMSO, the increase degree of the cortical hormone followed by stimulation of ACTH are shown in the following table:

TABLE 4

An increase degree of cortical hormone after administration of three salts of Formula (I) compound and stimulation of ACTH

| Compound | Increase degree of cortisol | Increase degree of corticosterone |
| --- | --- | --- |
| DMSO | 41.26 ± 28.64 | 30.24 ± 10.38 |
| Etomidate | 2.46 ± 0.87 | 2.80 ± 0.76 |
| Hydrochloride of formula (I) | 25.36 ± 14.77 | 18.14 ± 5.66 |
| Hydrobromide of formula (I) | 29.14 ± 11.86 | 12.36 ± 6.65 |
| Trifluoroacetate of formula (I) | 26.14 ± 13.89 | 13.64 ± 4.22 |

The results from the above experiments have shown that etomidate can significantly suppress the self-synthesis of adrenocortical hormone and make the cortex levels in the experimental dogs not increase after the stimulation by ACTH. After stimulation by ACTH, the cortical hormone increase in the groups of the dogs that had been respectively given the compounds of Formula (I) hydrochloride, hydrobromide, and trifluoroacetate was lower than that in the blank group of the dogs, but obviously higher than that in the positive medicine etomidate group of the dogs. Therefore, the inhibitory effect of the compound Formula (I) salts on cortical hormone had already been obviously reduced when compared with that of the control medicine etomidate.

The invention claimed is:
1. A trifluoroacetate salt of the N-substituted imidazole carboxylic ester chiral compound of Formula (I),

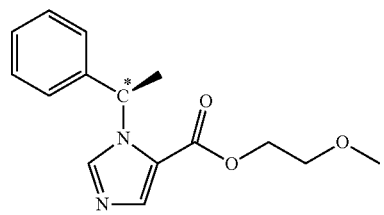

(I)

wherein the chiral carbon C* has a R form.

2. A process for preparation of the trifluoroacetate salt of the N-substituted imidazole carboxylic ester chiral compound of claim 1, comprising:
reacting, in a polar aprotic solvent and in the presence of a base, a chiral N-substituted imidazole carboxylic acid chiral compound of Formula (II) with a halide of Formula (III);
forming the compound of Formula (I), wherein the chiral carbon C* has the R form and X is a halogen,

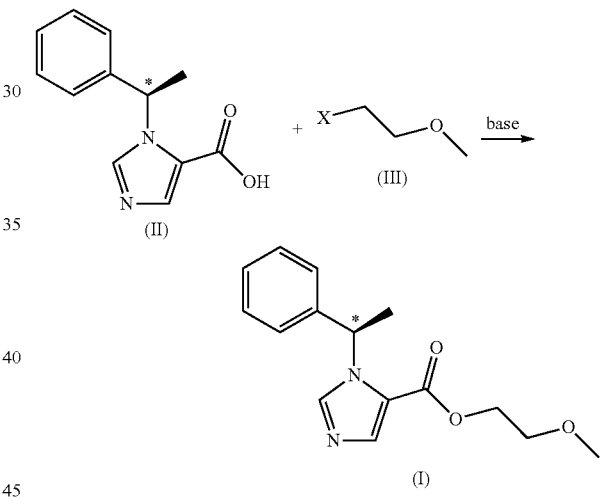

and further comprising combining the compound of Formula (I) with trifluoroacetic acid.

3. The process according to claim 2, wherein the polar aprotic solvent is DMF.

4. The process according to claim 2, wherein the base is an inorganic base.

5. The process according to claim 4, wherein the inorganic base is selected from the group consisting of alkali metal hydroxides and carbonates.

6. A method for inducing anesthesia, comprising administering a composition comprising the trifluoroacetate salt of the N-substituted imidazole carboxylic ester chiral compound of claim 1 to a mammal through intravenous or non-intravenous administration.

* * * * *